United States Patent
Habboushe

(10) Patent No.: US 11,013,751 B2
(45) Date of Patent: May 25, 2021

(54) COMPOSITIONS AND METHODS FOR TREATING MULTIPLE SCLEROSIS

(71) Applicant: Vitalis LLC, New York, NY (US)

(72) Inventor: Joseph Habboushe, New York, NY (US)

(73) Assignee: Vitalis LLC, New York, NY (US)

( * ) Notice: Subject to any disclaimer, the term of this patent is extended or adjusted under 35 U.S.C. 154(b) by 0 days.

(21) Appl. No.: 16/523,916

(22) Filed: Jul. 26, 2019

(65) Prior Publication Data

US 2020/0155577 A1 May 21, 2020

Related U.S. Application Data

(63) Continuation of application No. 15/922,729, filed on Mar. 15, 2018, now Pat. No. 10,398,712.

(60) Provisional application No. 62/594,493, filed on Dec. 4, 2017, provisional application No. 62/473,080, filed on Mar. 17, 2017.

(51) Int. Cl.
| | |
|---|---|
| *A61K 31/616* | (2006.01) |
| *A61K 31/225* | (2006.01) |
| *A61K 9/50* | (2006.01) |
| *A61K 31/194* | (2006.01) |
| *A61P 25/00* | (2006.01) |

(52) U.S. Cl.
CPC .............. *A61K 31/616* (2013.01); *A61K 9/50* (2013.01); *A61K 9/5026* (2013.01); *A61K 9/5042* (2013.01); *A61K 9/5073* (2013.01); *A61K 31/194* (2013.01); *A61K 31/225* (2013.01); *A61P 25/00* (2018.01); *A61K 2300/00* (2013.01)

(58) Field of Classification Search
CPC .. A61K 31/616; A61K 31/194; A61K 9/5026; A61K 9/5042; A61K 9/5073; A61K 31/225; A61K 9/50; A61K 2300/00; A61P 25/00
See application file for complete search history.

(56) References Cited

U.S. PATENT DOCUMENTS

| | | | |
|---|---|---|---|
| 8,652,520 B2 * | 2/2014 | Habboushe | A61K 9/0056 424/468 |
| 10,398,712 B2 | 9/2019 | Habboushe | |
| 2014/0234410 A1 | 8/2014 | Moodley et al. | |
| 2015/0352129 A1 | 12/2015 | Habboushe | |
| 2017/0042821 A1 | 2/2017 | Habboushe | |
| 2017/0056360 A1 | 3/2017 | Vaughn et al. | |

FOREIGN PATENT DOCUMENTS

| | | | |
|---|---|---|---|
| WO | WO 2013/119677 | | 8/2013 |
| WO | WO 2015/130998 | * | 9/2015 |

OTHER PUBLICATIONS

Sheikh et al. in Clinical Therapeutics 35 (10), 1582-1594 (2013) (Year: 2013).*
International Search Report and Written Opinion for PCT/US2018/022737 dated May 21, 2018. 14 pages.
Ohshiro, et al. Effects of salicylate on the pharmacokinetics of valproic acid after oral administration of sodium valproate in rats. Biogenic Amiens 2003; 17(4-6):401-407.
Willis, et al. A Study of the Effect of Aspirin on the Phamracokinetics of Oral and Intravenous Diclofenac Sodium. European Journal of Clinical Pharmacology. 1980; 18:415-418.
Extended European Search Report and Opinion dated Aug. 21, 2020 for EP Application No. 18767691.1. 12 pages.
Sheikh, et al. Tolerability and Pharmacokinetics of Delayed-Release Dimethyl Fumarate Administered With and Without Aspirin in Healthy Volunteers. Clinical Therapeutics. Oct. 2013; 35(10):1582-1594.e9.

* cited by examiner

*Primary Examiner* — Dennis Heyer
(74) *Attorney, Agent, or Firm* — Sheppard Mullin Richter & Hampton LLP

(57) ABSTRACT

Provided are compositions and methods for treating multiple sclerosis (MS). One embodiment of the disclosed method entails orally administering to a MS patient a first amount of aspirin and a second amount of fumaric acid or an ester or a salt thereof. In some embodiments, the aspirin is administered at from about 80 mg to about 500 mg per day and the fumaric acid or ester or salt thereof is administered at about 360 mg per day.

18 Claims, 1 Drawing Sheet

COMPOSITIONS AND METHODS FOR TREATING MULTIPLE SCLEROSIS

CROSS REFERENCE TO RELATED APPLICATIONS

This application is a continuation of U.S. application Ser. No. 15/922,729 filed Mar. 15, 2018, which claims the benefit under 35 U.S.C. § 119(e) of U.S. Provisional Application Ser. No. 62/473,080 filed Mar. 17, 2017, and Provisional Application Ser. No. 62/594,493, filed Dec. 4, 2017, the contents of which are incorporated by reference in its entirety into the present disclosure.

BACKGROUND

Multiple sclerosis (MS) is the most common autoimmune disorder affecting the central nervous system. In 2013, about 2.3 million people were affected globally with rates varying widely in different regions and among different populations. About 20,000 people died from MS in 2013, up from 12,000 in 1990. The disease usually begins between the ages of 20 and 50 and is twice as common in women as in men.

Multiple sclerosis was first described in 1868 by Jean-Martin Charcot. The name multiple sclerosis refers to the numerous scars that develop on the white matter of the brain and spinal cord. MS is a demyelinating disease in which the insulating covers of nerve cells in the brain and spinal cord are damaged. This damage disrupts the ability of parts of the nervous system to communicate, resulting in a range of signs and symptoms, including physical, mental, and sometimes psychiatric problems. Specific symptoms can include double vision, blindness in one eye, muscle weakness, trouble with sensation, or trouble with coordination. MS takes several forms, with new symptoms either occurring in isolated attacks (relapsing forms) or building up over time (progressive forms). Between attacks, symptoms may disappear completely; however, permanent neurological problems often remain, especially as the disease advances.

While the cause is not clear, the underlying mechanism is thought to be either destruction by the immune system or failure of the myelin-producing cells. Proposed causes for this include genetics and environmental factors such as being triggered by a viral infection. MS is usually diagnosed based on the presenting signs and symptoms and the results of supporting medical tests.

There is no known cure for multiple sclerosis. Treatments attempt to improve function after an attack and prevent new attacks. Medications used to treat MS, while modestly effective, can have side effects and be poorly tolerated. Physical therapy can help with a patient's ability to function.

It has been shown that dimethyl fumarate (DMF) and its metabolite, monomethyl fumarate (MMF), are effective treatments for relapse-remitting multiple sclerosis (RMMS). Both DMF and MMF activate the nuclear-factor-E2-related factor-2 (Nrf2) transcriptional pathway, which induces anti-inflammatory and neuroprotective modalities in RMMS patients. About 30% to 40% of treated individuals, however, suffer from cutaneous flush which is associated with both DMF and MMF. Such adverse effects, therefore, limit the use of DMF and MMF in treating MS.

SUMMARY

The present disclosure provides treatment regimens for diseases that can be suitably treated with fumaric acid of its ester or salt, such as dimethyl fumarate (DMF), monomethyl fumarate (MMF), or the combination thereof. Examples of such diseases include multiple sclerosis (MS), psoriasis, necrobiosis lipoidica, granuloma annulare, sarcoidosis, granulomatous and inflammatory skin disorders, lichen planus pityriasis rubra pilaris, chronic discoid lupus erythematosus, necrobiosis lipoidica, cheilitis granulomatosa, annular elastotic giant cell granuloma, malign melanoma, lupus erythematosus, aplopecia areata, hidradenitis suppurativa, other granulomatous and inflammatory skin disorders, other inflammatory disorders such as colitis, DNA damage in tumor, gastrointestinal ulceration, collagen type II degradation, and other immune modulated diseases. In some embodiments, the treatment methods enable the effective use of a daily dose of fumaric acid or an ester or salt thereof that is lower than their recommended use (e.g., 480 mg per day), without compromise of the treatment outcome.

It is discovered surprisingly that the methods and pharmaceutical compositions described herein may increase the bioavailability of the fumaric acid or an ester or salt thereof (e.g., dimethyl fumarate) such that a significantly lower dose can be administered (e.g., 420, 400 or 360 mg per day), without compromise of the treatment outcome. In addition, in some embodiments, the treatment methods allow a patient to tolerate a higher dose of fumaric acid or an ester or salt thereof, which higher dose may be required given the condition and other requirements of the patient.

In one embodiment, provided is a method of treating multiple sclerosis (MS) in a human patient in need thereof, comprising orally administering to the patient aspirin and fumaric acid or an ester or a salt thereof, wherein the aspirin is administered at from about 150 mg to about 650 mg (or from about 300 mg to about 500 mg) per day and the fumaric acid or ester or salt thereof is administered at about 300 mg to about 450 mg per day (or from about 340 mg to about 380 mg per day). The aspirin and the fumaric acid or ester or a salt thereof can be administered separately or together, concurrently or sequentially.

In some embodiments, the aspirin is formulated to dissolve in an oral cavity of a subject. In some embodiments, the fumaric acid or ester or salt thereof is formulated for dissolving in stomach, intestines, or further distal in the gastrointestinal tract of the subject.

Also provided, in one embodiment, is a method of treating multiple sclerosis (MS) in a human patient in need thereof, comprising orally administering to the patient one or more tablets each comprising a first portion comprising a first amount of aspirin and a second portion comprising a second amount of fumaric acid or an ester or a salt thereof, wherein the first portion is formulated to dissolve in an oral cavity of a subject, wherein the second portion is formulated for dissolving in stomach, intestines, or further distal in the gastrointestinal tract of the subject, and wherein the aspirin is administered at from about 150 (or 160, 170, 180, 190, 200, 210, 220, 230, 240, 250, 260, 270, 280, 290, 300, 310, 320, 330, 340, 350, 360, 370, 380, 390 or 400) mg to about 650 (or 410, 420, 430, 440, 450, 460, 470, 480, 490, 500, 510, 520, 530, 540, 550, 560, 570, 580, 590, 600, 610, 620, 630, or 640) mg per day and the fumaric acid or ester or salt thereof is administered at about 300 (or 300, 310, 320, 330, 340, 350, or 360) mg to about 450 (or 360, 370, 380, 390, 400, 410, 420, 430, 440, or 450) mg per day.

In some embodiments, the patient suffers from relapse-remitting MS (RRMS). In some embodiments, the patient has a history of non-compliance with a medication due to cutaneous flush or a gastrointestinal side effect.

In some embodiments, the second amount of the fumaric acid or ester or salt thereof is about 180 mg. In some embodiments, the first amount of aspirin is from about 80 mg to about 250 mg. In some embodiments, the second portion further comprises a third amount of aspirin. In some embodiments, the first amount of aspirin and the second amount of aspirin each is from about 40 mg to about 120 mg. In some embodiments, the second portion is enclosed in an enteric coating.

In some embodiments, the ester is dimethyl fumarate, monomethyl fumarate or combination thereof.

Pharmaceutical compositions are also provided. In some embodiments, the pharmaceutical composition is a fixed dose combination comprising aspirin and a fumaric acid or an ester or a salt thereof. In some embodiments, the pharmaceutical composition is a fixed dose combination comprising aspirin and dimethyl fumarate, optionally in combination with an additional fumaric acid or an ester or a salt thereof.

In some embodiments, the pharmaceutical composition comprises about 40 (or 50, 60, 70, 80, 90, 100, 110, 120, 130, 140, 150, 160, 170, 180, or 190) mg to about 250 (or 210, 220, 230, or 240) mg of aspirin and about 150 (or 160, 165, 170, 175, 180, or 185) mg to about 190 (or 180, 185, 195, 200, 210, 220, 225, or 230) mg of fumaric acid or an ester or a salt thereof. In some embodiments, the pharmaceutical composition comprises about 300 (or 310, 320, 330, 340, 350, 360, 370, 380, 390 or 400) mg to about 500 (or 410, 420, 430, 440, 450, 460, 470, 480, or 490) mg of aspirin and about 340 (or 300, 310, 320, 330, 350, or 360) mg to about 380 (or 360, 370, 380, 390, 400, 410, 420, 430, 440, or 450) mg of fumaric acid or an ester or a salt thereof.

In some embodiments, the pharmaceutical compositions described herein are formulated as a tablet. In some embodiments, the pharmaceutical compositions described herein are formulated as a capsule comprising the aspirin and a fumaric acid or an ester or a salt thereof. In some embodiments, the pharmaceutical compositions described herein are formulated as a capsule comprising the aspirin and a fumaric acid or an ester or a salt thereof, wherein the aspirin and fumaric acid or an ester or a salt thereof are each formulated as a microsphere. In some embodiments, the aspirin is present in a first portion formulated to dissolve in an oral cavity of a subject, and the fumaric acid or ester or salt thereof is present in a second portion formulated for dissolving in stomach, intestines, or further distal in the gastrointestinal tract of the subject.

In some embodiments, the aspirin is present in a first portion formulated to dissolve in an oral cavity of a subject, and a second portion formulated for dissolving in stomach, intestines, or further distal in the gastrointestinal tract of the subject. In some embodiments, the pharmaceutical compositions described herein are formulated as a capsule comprising the aspirin and a fumaric acid or an ester or a salt thereof, wherein the aspirin and fumaric acid or an ester or a salt thereof are each formulated as a microsphere contained within a capsule shell, and a second portion of aspirin is present as a coating on the capsule shell and is formulated to dissolve in an oral cavity of a subject. By administering this particular dosage form, it is contemplated that the effective dose of DMF can be reduced, thus reducing and/or relieving one or more side effects of DMF.

In one embodiment, provided is a method of treating multiple sclerosis (MS) in a human patient in need thereof, comprising orally administering to the patient aspirin and fumaric acid or an ester or a salt thereof, wherein the aspirin is administered at from about 300 mg to about 500 mg per day and the fumaric acid or ester or salt thereof is administered at about 580 mg to about 620 mg per day. In some embodiments, the aspirin is formulated to dissolve in an oral cavity of a subject. In some embodiments, the fumaric acid or ester or salt thereof is formulated for dissolving in stomach, intestines, or further distal in the gastrointestinal tract of the subject. In some embodiments, the aspirin and the fumaric acid or ester or salt thereof are administered concurrently.

Also provided, in one embodiment, is a method of treating multiple sclerosis (MS) in a human patient in need thereof, comprising orally administering to the patient one or more tablets each comprising a first portion comprising a first amount of aspirin and a second portion comprising a second amount of fumaric acid or an ester or a salt thereof, wherein the first portion is formulated to dissolve in an oral cavity of a subject, wherein the second portion is formulated for dissolving in stomach, intestines, or further distal in the gastrointestinal tract of the subject, and wherein the aspirin is administered at from about 150 mg to about 650 mg per day and the fumaric acid or ester or salt thereof is administered at about 570 mg to about 630 mg per day, or about 300 to about 450 mg per day, or about 300 to about 400 mg per day, or about 350 to about 400 mg per day, or about 360 mg per day.

In some embodiments, the patient suffers from relapse-remitting MS (RRMS). In some embodiments, the patient suffers from secondary progressive multiple sclerosis (SPMS).

Also provided, in one embodiment, is a method of treating psoriasis in a human patient in need thereof, comprising orally administering to the patient one or more tablets each comprising a first portion comprising a first amount of aspirin and a second portion comprising a second amount of fumaric acid or an ester or a salt thereof, wherein the first portion is formulated to dissolve in an oral cavity of a subject, wherein the second portion is formulated for dissolving in stomach, intestines, or further distal in the gastrointestinal tract of the subject, and wherein the aspirin is administered at from about 150 mg to about 650 mg per day and the fumaric acid or ester or salt thereof is administered at about 570 mg to about 630 mg per day, or about 300 to about 450 mg per day, or about 300 to about 400 mg per day, or about 350 to about 400 mg per day, or about 360 mg per day.

In addition to multiple sclerosis and psoriasis, fumaric acid or ester or salt thereof can also be used for treating other diseases and conditions such as motor neuron disease, neurodegenerative diseases, autoimmune diseases, inflammatory diseases, sepsis, and skin diseases or conditions.

A motor neuron disease a neurological condition that selectively affects motor neurons. Examples include amyotrophic lateral sclerosis (ALS), hereditary spastic paraplegia (HSP), primary lateral sclerosis (PLS), progressive muscular atrophy (PMA), progressive bulbar palsy (PBP) and pseudobulbar palsy.

Neurodegenerative diseases are results of progressive loss of structure or function of neurons, including death of neurons. Examples include amyotrophic lateral sclerosis, Parkinson's, Alzheimer's, and Huntington's, which occur as a result of neurodegenerative processes.

Non-limiting examples of autoimmune or inflammatory disease include Parkinson's disease, arthritis, rheumatoid arthritis, multiple sclerosis, psoriasis, psoriatic arthritis, Crohn's disease, inflammatory bowel disease, ulcerative colitis, lupus, systemic lupus erythematous, juvenile rheumatoid arthritis, juvenile idiopathic arthritis, Grave's disease, Hashimoto's thyroiditis, Addison's disease, celiac disease, dermatomyositis, multiple sclerosis, myasthenia gravis, pernicious anemia, Sjogren syndrome, type I diabetes, vasculitis, uveitis, atherosclerosis and ankylosing spondylitis.

Skin diseases are various skin problems, from small red bumps on the skin to widespread rashes. Some skin conditions can be unsightly but harmless, while others may be contagious. Many skin conditions are also itchy or painful. The presently disclosed compositions and methods are suitable for treating these diseases and the symptoms. Non-limiting examples of symptoms include itch, swelling, redness, rash, flaky, scaly skin, blisters, oozing and bumps or growths.

In some embodiments, the second amount of the fumaric acid or ester or salt thereof is about 300 mg. In some embodiments, the first amount of aspirin is from about 80 mg to about 250 mg. In some embodiments, the second portion further comprises a third amount of aspirin. In some embodiments, the first amount of aspirin and the second amount of aspirin each is from about 80 mg to about 120 mg. In some embodiments, the first portion further comprises a water-soluble sugar or sugar substitute. In some embodiments, the second portion is enclosed in an enteric coating. In some embodiments, the ester is dimethyl fumarate, monomethyl fumarate or combination thereof. In some embodiments, the monomethyl fumarate is hydrogen monomethyl fumarate or a salt thereof (e.g., $Na^+$, $K^+$, $Ca^{2+}$, $Zn^{2+}$, $Mg^{2+}$, $Fe^{2+}$). In some embodiments, the monomethyl fumarate is hydrogen monomethyl fumarate.

Pharmaceutical compositions are also provided, for example, suitable for once daily, twice daily, or three times daily administration. In one embodiment, the composition comprises about 100 (or 110, 120, 130, 140, 150, 160, 170, 180, 190, or 200) mg to about 250 (or 200, 210, 220, 230, or 240) mg of aspirin and about 170 (or 175, 180, 185, or 190) mg to about 220 (or 185, 190, 195, 200, 205, 210, or 215) mg of fumaric acid or an ester or a salt thereof. In one embodiment, the composition comprises about 150 (or 160, 170, 180, or 190) mg to about 250 (or 210, 220, 230, or 240) mg of aspirin and about 285 (or 270, 270, 280, 290, 295, or 300) mg to about 315 (or 300, 305, 310, 320, or 325) mg of fumaric acid or an ester or a salt thereof. In one embodiment, the composition comprises about 300 (or 310, 320, 330, 340, 350, 360, 370, 380, 390 or 400) mg to about 500 (or 410, 420, 430, 440, 450, 460, 470, 480, or 490) mg of aspirin and about 570 (or 560, 565, 575, 580, 590 or 595) mg to about 630 (or 605, 610, 515, 620, 625, 635, or 640) mg of fumaric acid or an ester or a salt thereof. In one embodiment, the composition comprises about 40 (or 20, 30, 40, 50, 60, 70, 80, 90, 100 or 120) mg to about 500 (or 410, 420, 430, 440, 450, 460, 470, 480, or 490) mg of aspirin and about 120 (or 130, 140, 150, 160, 170, 180, 190, 200, 210 or 220) mg to about 240 (or or 210, 220, 230, or 240) mg of fumaric acid or an ester or a salt thereof.

DETAILED DESCRIPTION

Figure 1:
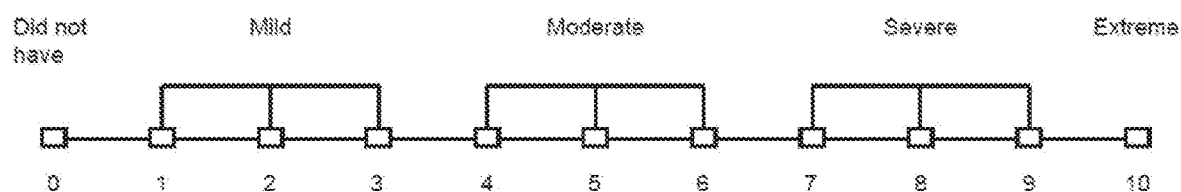
FIG. 1 is an example of the scale that was used to rate the assessment of Question 1 in Example 4.

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Relapse-remitting multiple sclerosis," or RRMS, is a type of MS of which symptoms can appear suddenly and be severe and can then go quiet for months or years. Between flare-ups, the disease tends not to progress or progresses relatively slowly, and symptoms may disappear.

"Secondary-progressive multiple sclerosis," or SPMS, is a MS condition in which the disease tends to progress steadily. This can happen with or without relapses. Many patients with RRMS may transition to SPMS at some point in the course of their disease.

"Fumaric acid" is the chemical compound with the formula $HO_2CCH=CHCO_2H$. The "salts and esters" of fumaric acid are known as fumarates, and include any ester (e.g., mono ester hydrogen fumarate or salt thereof or diester of fumaric acid), such as dimethyl fumarate (DMF) and monomethyl fumarate (MMF). The fumaric acid can comprise a mixture of DMF, also three monoethyl hydrogen fumarates or salt thereof (calcium, magnesium, and zinc salts) (e.g., Fumaderm®). The fumaric acid can comprise ALKS 8700 ("a MMF molecule" which is a prodrug to MMF).

Dimethyl fumarate (DMF) is the dimethyl ester of fumaric acid, having a chemical name of dimethyl (E)-butenedioate. DMF and its metabolite, monomethyl fumarate (MMF), were initially recognized as effective hypoxic cell radiosensitizers. They are also used as oral therapy for psoriasis. Other diseases, such as necrobiosis lipoidica, granuloma annulare, and sarcoidosis may also be suitably treated with DMF and MMF.

In a non-medical setting, DMF is applied as a biocide to prevent growths of mold during storage or transport in a humid climate. However, due to incidences of allergic reactions after skin contact the European Union banned DMF in consumer products since 1998, and since January 2009 the import of products containing DMF was also banned. Medical use of DMF also is known to come with associated side effects, such as progressive multifocal leukoencephalopathy, which can be serious. Another side effect associated with the use of DMF or MMF is the flushing, which has been reported to cause non-compliance of patients.

A commercial form of DMF for treating MS is Tecfidera®. According to the drug label, the starting dose for Tecfidera® is 120 mg twice a day orally. After 7 days, the dose should be increased to the maintenance dose of 240 mg twice a day orally. Temporary dose reductions to 120 mg twice a day may be considered for individuals who do not tolerate the maintenance dose. Higher doses of Tecfidera® are not recommended.

It is a surprising and unexpected discovery of the instant inventor that administration of both aspirin and fumaric acid or its ester or salt such as DMF and MMF achieves increased treatment efficacy and reduced side effects as compared to the fumarate alone. Such a dual administration, therefore, makes it possible to use a lower dose (e.g., 420, 400 or 360 mg per day) of fumaric acid of the ester or salt thereof, as compared to the conventional commercial dose (e.g., 480 mg per day), to achieve the same efficacy as the conventional dose would but with greatly reduced side effects.

The impact of aspirin on the bioavailability of DMF has been evaluated previously and acknowledged by the US FDA. In Sheikh et al., *Clin Ther.* 2013; 35:1582-94, for example, the authors observed that pretreatment with 325 mg aspirin for 4 days reduced flushing incidence and intensity but did not affect gastrointestinal events or the pharmacokinetic profile of DMF (abstract). In other words, aspirin pretreatment did not change the bioavailability of the DMF. Accordingly, the present discovery that concomitant administration of aspirin increased the bioavailability of DMF by about 5% is necessarily surprising and unexpected.

Such a surprising and unexpected discovery that the dual administration increases the bioavailability of the fumarate (e.g., DMF) makes it possible to use a lower dose (e.g., 420, 400 or 360 mg per day) while achieving the same or substantially similar efficacy as compared to the conventional commercial dose (e.g., 480 mg per day), to achieve the same efficacy as the conventional dose. On the other hand, this dual formulation allows administration of a higher dose (e.g., 600 mg per day) of fumaric acid of the ester or salt thereof so that patients who desire such high doses can avoid or suffer reduced undesirable side effects such as flushing. The dual administration can be sequential administration or concurrent administration of two or more separate compositions, or administration of a composition that includes two or more different ingredients.

In some embodiments, a co-formulation is disclosed. In some aspects, the aspirin and fumaric acid of the ester or salt thereof are in separate portions in the co-formulation, such as a tablet. In some aspects, the separate portions are formulated similarly and in other aspects, the aspirin portion is formulated in a dissolvable fashion (dissolvable portion) and the fumaric acid portion is formulated as a swallowable fashion (swallowable portion). In some aspects, the swallowable portion also contains an amount of aspirin, which is shown to further enhance the effect of the dissolvable aspirin in a synergistic fashion.

In some embodiments, a similarly structured co-formulation is disclosed that includes aspirin and therapeutic agent having a niacin-mediated flushing side effect. The term "therapeutic agent having a niacin-mediated flushing side effect," as used herein, refers to a group of drugs that activate the nicotinic acid receptor GPR109a, resulting in flushing symptoms commonly observed for patients taking niacin. Sometimes, such agents are also referred to as "nicotinic acid receptor agonists" or "GPR109a agonists." Non-limiting examples of such therapeutic agents include niacin, nicotyinyl alcohol, acipimox, acifran, newer GPR109a agonists, hydroxybutyrate, and fumarates (e.g., dimethyl fumarate, mono-ethyl fumarate, diethyl fumarate).

Structure-activity studies have shown common structural features of GPR109a agonists. Some of the GPR109a agonists have a carcoxyl group, like in niacin. Another group are anthranilic acid analogs. More of such structural elements are discussed in Boatman et al. *J. Med. Chem.* 2008; 51(24):7653-62.

In some embodiments, aspirin can be substituted with a non-steroidal anti-inflammation drug (NSAID). Non-limiting examples of NSAIDs include aspirin, celecoxib, diclofenac, diflunisal, etodolac, ibuprofen, indomethacin, ketoprofen, ketorolac, nabumetone, naproxen, oxaprozin, piroxicam, salsalate, sulindac, and tolmetin.

A "dissolvable portion" as used herein refers to a portion of a drug form that is formulated to dissolve in an oral cavity of a subject. A dissolvable portion, in one embodiment, is pulverizable which can be dispersed in the oral cavity by masticating, sucking, dissolving or other common means, thereby releasing its active ingredient into the oral cavity where it enters the circulatory system by traversing the buccal mucosa. Other embodiments of dissolvable portions are also provided below in the present disclosure.

A "swallowable portion" is relative to the dissolvable portion and can be harder than the dissolvable portion. Therefore, the swallowable portion is more readily swallowed by the subject and releases the active ingredient by dissolving it in stomach, intestines, or further distal in the gastrointestinal (GI) tract of the subject.

The dissolvable portion and the swallowable portion, in some embodiments, are side by side in a tablet but with different physical or chemical properties. In some embodiments, the intraoral is placed outside of the swallowable portion to form a bi-layer tablet.

In the context of the present disclosure, the use of the term hard or swallowable in reference to the dissolvable portion is used to connote that the swallowable portion is not pulverized by the force and can withstand the force of masticating or chewing that effectively pulverizes the outer layer of the pharmaceutical composition of the present disclosure. In one embodiment, the swallowable portion is chew-resistant. Further, in referring to the swallowable portion as being ingestible, it is meant that the swallowable portion is capable of being taken up and absorbed by one or more portions of the gastrointestinal tract, stomach, intestines or a further distal of the gastrointestinal tract. The swallowable portion of the combination tablet may be conventionally covered with one or more layers of coatings to permit a timed release of the active contained therein following ingestion by a subject. The present disclosure contemplates a release profile of the ingested core particle of from 30 minutes to 24 hours.

In the context of the present disclosure, the term pulverizable or easily pulverizable refers to a portion of a material that is ground or dispersed into small particles within the oral cavity by gentle pressure generated by chewing or masticating the layer to be ground. There is no intent to imply any particular size or fineness of the resulting particles, as it is contemplated herein that it is only required that the pulverized material release a therapeutic agent within the oral cavity.

The term masticating or chewing, in the context of the present disclosure, is meant to signify that the pulverizing or grinding is being performed by a patient's or subject's teeth, or gums. A specific embodiment of the combination pill may cause the first bite(s) to rupture or dislodge the outer layer thereby releasing it from the central core and can then be chewed. There is no intent to signify any particular degree of force required or generated by the masticating teeth or gums. The requirement is that the force actually used to produce the pulverized granules, particles, powder and the like, is sufficient to disrupt the dissolvable portion of the present disclosure while leaving the swallowable portion intact.

The term sucking, dissolving or other common means, in the context of the present disclosure, is meant to signify that the intraoral or pulverizable portion can be absorbed in the oral cavity through use of the tongue, gums, cheeks, saliva and combinations thereof, over a period of time. A specific embodiment of the combination pill causes the intraoral or pulverizable portion to dissolve in the oral cavity over a period of 5 minutes, while the combination pill is held in the oral cavity, through interaction with saliva. The requirement is that interaction with the tongue, gums, cheeks, saliva and combinations thereof by sucking, dissolving or other common means, is sufficient to disrupt the outer layer of the pharmaceutical composition of the present disclosure while leaving the swallowable portion intact.

For the purpose of this description, the term intact does not require that the swallowable portion remain in one piece. Instead, it signifies that at least 50% of the swallowable portion is swallowed, but preferably that 75% of the swallowable portion material is swallowed; even more preferably that approximately 75% to about 85% of the swallowable portion material is swallowed, and most preferably, from about 85% to about 95% of the swallowable portion material is swallowed, and most particularly, that greater than 95% of the swallowable portion material is swallowed.

The buccal mucosa is meant to refer to the epithelium lining the oral cavity, including the sublingual region. The buccal mucosa further includes the sub-epithelial tissue; i.e., the tissue and macromolecular layers that accumulate underneath the epithelium. The sub-epithelial tissue includes, inter alia, connective tissue cells (fibroblasts, adipocytes, lymphocytes, and the like), extracellular matrix, basement membrane, smooth muscle, and vascular elements, etc. The buccal mucosa is a highly vascular tissue, and therefore a desirable route of entry into the general circulation.

In one embodiment, the present disclosure provides a method of treating multiple sclerosis (MS) in a human patient in need thereof. In some embodiments, the disease or condition being treated is one or more of psoriasis, necrobiosis lipoidica, granuloma annulare, sarcoidosis, granulomatous and inflammatory skin disorders, lichen planus pityriasis rubra pilaris, chronic discoid lupus erythematosus, necrobiosis lipoidica, cheilitis granulomatosa, annular elastotic giant cell granuloma, malign melanoma, lupus erythematosus, aplopecia areata, hidradenitis suppurativa, other granulomatous and inflammatory skin disorders, other inflammatory disorders such as colitis, DNA damage in tumor, gastrointestinal ulceration, collagen type II degradation, and other immune modulated diseases.

The method entails, in one embodiment, orally administering to the patient a first amount of aspirin and a second amount of fumaric acid or an ester or a salt thereof. In some embodiments, the aspirin is administered at from about 300 mg to about 500 mg per day and the fumaric acid or ester or salt thereof is administered at about 340 mg to about 380 mg per day.

The method entails, in one embodiment, orally administering to the patient one or more tablets each comprising a first portion comprising a first amount of aspirin and a second portion comprising a second amount of fumaric acid or an ester or a salt thereof, wherein the first portion is formulated to dissolve in an oral cavity of a subject, wherein the second portion is formulated for dissolving in stomach, intestines, or further distal in the gastrointestinal tract of the subject, and wherein the aspirin is administered at from about 300 mg to about 500 mg per day and the fumaric acid or ester or salt thereof is administered at about 340 mg to about 380 mg per day.

In some embodiments, the daily dose of the fumaric acid or ester or salt thereof is about 350 mg to about 370 mg, or about 355 mg to about 365 mg, or about 360 mg.

In some aspects, the daily administration is twice daily, and each administration is with one or two tablets. In one aspect, the second portion of each tablet, also referred to as the swallowable portion, contains about 170 mg to about 190 mg fumaric acid or an ester or salt thereof. In one aspect, the second portion of each tablet, also referred to as the swallowable portion, contains about 175 mg to about 185 mg fumaric acid or an ester or salt thereof. In one aspect, the second portion of each tablet, also referred to as the swallowable portion, contains about 180 mg fumaric acid or an ester or salt thereof.

In one aspect, the first portion of each tablet, also referred to as the dissolvable portion, contains about 150 mg to about 250 mg aspirin, or alternatively about 175 mg to about 225 mg aspirin, or about 200 mg aspirin. In some embodiments, the first portion contains about 75 mg to about 125 mg aspirin, or alternatively about 90 mg to about 110 mg aspirin, or about 100 mg aspirin, and meanwhile the second portion further contains about 75 mg to about 125 mg aspirin, or alternatively about 90 mg to about 110 mg aspirin, or about 100 mg aspirin, such that the total amount of aspirin in each tablet can still be about 150 mg to about 250 mg.

In some embodiments, the patient suffers from relapse-remitting MS (RRMS), a relatively common form of MS. In some embodiments, the patient has a history of non-compliance with a medication due to cutaneous flush or a gastrointestinal side effect. "Non-compliance" as used herein refers to a patient's failure, of at least one time, to take the DMF/MMF medication due to complaint of flushing. In some embodiments, the patient has suspended taking DMF/MMF for at least 1 week, 2 weeks, 1 month, 2 months, 3 months, or 6 months.

In one embodiment, the present disclosure provides a method of treating multiple sclerosis (MS) in a human patient in need thereof.

In some embodiments, the disease or condition being treated is one or more of psoriasis, necrobiosis lipoidica, granuloma annulare, sarcoidosis, granulomatous and inflammatory skin disorders, lichen planus pityriasis rubra pilaris, chronic discoid lupus erythematosus, necrobiosis lipoidica, cheilitis granulomatosa, annular elastotic giant cell granuloma, malign melanoma, lupus erythematosus, aplopecia areata, hidradenitis suppurativa, other granulomatous and inflammatory skin disorders, other inflammatory disorders such as colitis, DNA damage in tumor, gastrointestinal ulceration, collagen type II degradation, and other immune modulated diseases.

The method entails, in one embodiment, orally administering to the patient a first amount of aspirin and a second amount of fumaric acid or an ester or a salt thereof. In some embodiments, the aspirin is administered at from about 300 mg to about 500 mg per day and the fumaric acid or ester or salt thereof is administered at about 570 mg to about 630 mg per day.

The method entails, in one embodiment, orally administering to the patient one or more tablets each comprising a first portion comprising a first amount of aspirin and a second portion comprising a second amount of fumaric acid or an ester or a salt thereof, wherein the first portion is formulated to dissolve in an oral cavity of a subject, wherein the second portion is formulated for dissolving in stomach, intestines, or further distal in the gastrointestinal tract of the subject, and wherein the aspirin is administered at from about 300 mg to about 500 mg per day and the fumaric acid or ester or salt thereof is administered at about 570 (or 575, 580, 585, 590, or 595) mg to about 630 (or 605, 610, 615, 620 or 625) mg per day.

In some embodiments, the daily dose of the fumaric acid or ester or salt thereof is about 590 mg to about 610 mg, or about 595 mg to about 605 mg, or about 600 mg.

In some aspects, the daily administration is once, twice or three times daily, and each administration is with one or two tablets. In one aspect, the second portion of each tablet, also referred to as the swallowable portion, contains about 290 mg to about 310 mg fumaric acid or an ester or salt thereof. In one aspect, the second portion of each tablet, also referred to as the swallowable portion, contains about 295 mg to about 305 mg fumaric acid or an ester or salt thereof. In one aspect, the second portion of each tablet, also referred to as the swallowable portion, contains about 300 mg fumaric acid or an ester or salt thereof.

In one aspect, the first portion of each tablet, also referred to as the dissolvable portion, contains about 150 mg to about 250 mg aspirin, or alternatively about 175 mg to about 225 mg aspirin, or about 200 mg aspirin. In some embodiments, the first portion contains about 75 mg to about 125 mg aspirin, or alternatively about 90 mg to about 110 mg aspirin, or about 100 mg aspirin, and meanwhile the second portion further contains about 75 mg to about 125 mg aspirin, or alternatively about 90 mg to about 110 mg aspirin, or about 100 mg aspirin, such that the total amount of aspirin in each tablet can still be about 150 mg to about 250 mg.

In some embodiments, the patient has been treated with fumaric acid or an ester or salt thereof but the treatment is considered inadequate. In some embodiments, the patient suffers from relapse-remitting MS (RRMS). In some embodiments, the patient suffers from secondary progressive multiple sclerosis (SPMS).

Example Co-Formulations

Pharmaceutical formulations are provided, in some embodiments. The formulations may include aspirin at a suitable dose and form and a fumaric acid or an ester or a salt thereof at a suitable dose and form. In some embodiments, the formulation includes at last about 20, 30, 40, 50, 60, 70, 80, 90, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 mg aspirin. In some embodiments, the formulation includes not more than about 500, 490, 480, 470, 460, 450, 440, 430, 420, 410, 400, 390, 380, 370, 360, 350, 340, 330, 325, 320, 315, 310, 305, 300, 295, 290, 285, 280, 275, 260, 255, 250, 245, 240, 235, 230, 225, 220, 215, 210, 205, 200, 190, 180, 170, 160, or 150 mg aspirin.

In some embodiments, the formulation includes at least about 80, 90, 100, 120, 125, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 510, 520, 530, 540, 550, 560, 570, 580, 590, or 600 mg of a fumaric acid or an ester or a salt thereof. In some embodiments, the formulation include not more than about 600, 590, 580, 570, 560, 55, 540, 530, 520, 510, 500, 490, 480, 470, 460, 450, 440, 430, 420, 410, 400, 390, 380, 370, 360, 350, 340, 330, 325, 320, 315, 310, 305, 300, 295, 290, 285, 280, 275, 260, 255, 250, 245, 240, 235, 230, 225, 220, 215, 210, 205, 200, 195, 190, 185, 180, 175, 170, 165, 160, 155, or 150 mg of a fumaric acid or an ester or a salt thereof.

In some embodiments, the fumaric acid or an ester or a salt thereof is dimethyl fumarate, optionally in combination with an additional fumaric acid or an ester or a salt thereof. In some embodiments, the additional fumaric acid or an ester or a salt thereof is monomethyl fumarate or a salt thereof (e.g., $Na^+$, $K^+$, $Ca^{2+}$, $Zn^{2+}$, $Mg^{2+}$, $Fe^{2+}$). In some embodiments, the monomethyl fumarate is hydrogen monomethyl fumarate. In some embodiments, the pharmaceutical composition consists essentially of an effective amount of aspirin and an effective amount of dimethyl fumarate.

In some embodiments, the pharmaceutical composition comprises from about 80 mg to about 380 mg of the fumaric acid or ester or salt thereof. In some embodiments, the pharmaceutical composition comprises from about 80 mg to about 380 mg of the dimethyl fumarate. In some embodiments, the pharmaceutical composition comprises from about 30 mg to about 500 mg of aspirin. In some embodiments, the pharmaceutical composition comprises from about 150 mg to about 500 mg of aspirin. In some embodiments, the pharmaceutical composition comprises from about 30 mg to about 500 mg of aspirin and from about 80 mg to about 380 mg of a fumaric acid or an ester or a salt thereof. In some embodiments, the pharmaceutical composition comprises from about 150 mg to about 500 mg of aspirin and from about 80 mg to about 380 mg of a fumaric acid or an ester or a salt thereof.

In some embodiments, the pharmaceutical compositions described herein are formulated as a capsule comprising aspirin and a fumaric acid or an ester or a salt thereof, wherein the aspirin and fumaric acid or an ester or a salt thereof are each formulated as a microsphere contained within a capsule shell, and a second portion of aspirin is present as a coating on the capsule shell and is formulated to dissolve in an oral cavity of a subject.

In some embodiments, the pharmaceutical composition, or dosage form, provided herein comprises aspirin and a fumaric acid or an ester or a salt thereof, wherein the aspirin and fumaric acid or an ester or a salt thereof are each individually formulated as enterically coated microspheres which are contained within a capsule shell. In some embodiments, the capsule may also be coated with a second portion of aspirin formulated to dissolve in an oral cavity of a subject. In some embodiments, the total dose of aspirin of the capsule (i.e., the combined amount present within the capsule in combination with the aspirin present as a coating on the capsule shell) is about 20 mg to about 500 mg, or about 20 mg to about 325 mg, or about 20 mg, or about 25 mg, or about 30 mg, or about 40 mg, or about 50 mg, or about 60 mg, or about 70 mg, or about 75 mg, or about 80 mg, or about 90 mg, or about 100 mg, or about 110 mg, or about 120 mg, or about 130 mg, or about 140 mg, or about 150 mg, or about 160 mg, or about 170 mg, or about 180 mg, or about 190 mg, or about 200 mg, or about 210 mg, or about 220 mg, or about 230 mg, or about 240 mg, or about 250 mg, or about 260 mg, or about 270 mg, or about 280 mg, or about 290 mg, or about 300 mg, or about 310 mg, or about 315 mg, or about 320 mg, or about 325 mg.

In some embodiments, the total dose of aspirin of the capsule is present in about a 1:1 ratio between the aspirin microspheres within the capsule and the aspirin present as a coating on the capsule shell. In some embodiments, the dose of aspirin present as microspheres within the capsule is about 20 mg, or about 30 mg, or about 40 mg, or about 50 mg, or about 60 mg, or about 70 mg, or about 75 mg, or about 80 mg. In some embodiments, the dose of aspirin present as a coating on the capsule shell is about 20 mg, or about 25 mg, or about 30 mg, or about 40 mg, or about 50 mg, or about 60 mg, or about 70 mg, or about 75 mg, or about 80 mg.

The microspheres described herein may also include non-spherical microparticles, such as oblong or cylindrical microparticles.

In some embodiments, the microspheres described herein have an average particle size of less than about 7 mm, or less than about 6 mm, or less than about 5 mm, or less than about 4 mm, or less than about 3 mm, or less than about 2 mm, or less than about 1.7 mm, or less than about 1.6 mm, or less than about 1.5 mm, or less than about 1.4 mm, or less than about 1.3 mm, or less than about 1.2 mm, or less than about 1.1 mm, or less than about 1.0 mm, or less than about 900 µm, or less than about 850 µm, or less than about 800 µm, or less than about 750 µm, or less than about 700 µm, or less than about 650 µm, or less than about 600 µm, or less than about 550 µm, or less than about 500 µm, or less than about 450 µm, or less than about 300 µm. In some embodiments, the particle size ranges from about 900 µm to about 2,000 µm, or from about 850 µm to about 1.7 mm, or from about 1.0 mm to 1.5 mm.

In some embodiments, the microspheres comprise an enteric coating such that the API (aspirin or fumaric acid or an ester or a salt thereof (e.g., DMF)) is released in the gastrointestinal tract (e.g., the small intestine). In some embodiments, the enteric coating on the microspheres is formulated or applied such that the aspirin is released in the gastrointestinal tract (e.g., the small intestine) at substantially the same time as the fumaric acid or an ester or a salt thereof (e.g., DMF). In some embodiments, the enteric coating on the microspheres is formulated or applied such that the aspirin is released in the gastrointestinal tract (e.g., the small intestine) just prior to (e.g., 1-5, 1-10, 1-15, or 1-20 minutes) the fumaric acid or an ester or a salt thereof (e.g., DMF). Accordingly, in some embodiments, the enteric coating on the aspirin microspheres is thinner than the enteric coating on the fumaric acid or an ester or a salt thereof (e.g., DMF) microspheres.

It is contemplated that by co-administering the aspirin and fumaric acid or an ester or a salt thereof (e.g., DMF) to the patient in such a way that the aspirin is absorbed within less than about 5 minutes (or less than about 10 minutes, 15 minutes, 20 minutes, 25 minutes or 30 minutes) of, or substantially simultaneously to, the fumaric acid or an ester or a salt thereof (e.g., DMF), the bioavailability of the fumaric acid or an ester or a salt thereof (e.g., DMF) will be enhanced such that the therapeutically effective dose is about 480 mg/day or less, or at least about 360 mg/day, or about 360 mg/day, or about 380 mg/day, or about 400 mg/day, or about 410 mg/day, or about 420 mg/day, or between about 360 mg/day and 420 mg/day, or between about 360 mg/day and 480 mg/day.

In some embodiments, the microspheres described herein comprise about 80% w/w, or about 75% w/w, or about 70% w/w, or about 65% w/w active ingredient (i.e., aspirin or fumaric acid or an ester or a salt thereof).

In one embodiment, an example co-formulation has a chewable outer layer as the dissolvable portion, such that it can be absorbed quickly. This chewable layer may be adhered directly to the inner layer (the swallowable portion), or it may be such designed that when it is bitten lightly (e.g. with minimal force, such as the force needed to chew a banana), this outer chewable layer breaks off into many pieces within the mouth, and can be chewed and thus absorbed, leaving the hard inner layers in the mouth to be swallowed. By making the chewable layer "crumble" in such a way, the patient will avoid biting hard through the hard inner layer of the tablet, which could be uncomfortable if the inner tablet is very hard, or could damage the integrity of the inner tablet, allowing it to be absorbed earlier than desired.

This may be similar to eating a cherry, where one bites the outer layer off and eats it, but does not bite too hard to chip their tooth on the hard inner pit. However, in the inventive tablet the patient would then swallow the inner tablet, instead of spitting out the cherry pit.

The outer chewable layer can be formulated, e.g., with a water soluble sugar and/or a sugar substitutes. Suitable water-soluble sugars and/or sugar substitutes are glucose, maltose, sucrose, dextrose, fructose, sorbitol, mannitol or other types of natural or artificial sweeteners. Mixtures of various sugars or sugar substitutes are also suitable.

The chewable layer can also be formulated with, e.g., a gel forming agent. Examples of such suitable gel formers are xanthan gum, methylcelluloses such as sodium carboxymethylcellulose or hydroxypropylmethylcellulose, hydroxyethylcellulose, hydroxypropylcellulose, alginates, tragacanth or edible starch. These substances are all commercially available and usually meet the purity requirements and quality regulations for pharmaceutical products. All such gel formers and coatings contemplated are GRAS (generally regarded as safe).

Wetting agents and lubricants such as sodium lauryl sulfate, as well as coloring agents, flavoring agents, sweetening agents (including other nonnutritive sweeteners), tableting agents, stabilizers, antioxidants, cooling agents, and preservatives, can also be present.

A binding agent can also be present such as cellulose, cellulosic derivatives, polyvinyl pyrrolidone, starch, modified starch, and mixtures thereof, and, in particular, microcrystalline cellulose.

One example of a manufacturing technique to formulate the chewable component over the solid dosage form is compression coating. The compression coating can be prepared by, e.g., a Manesty Dry-Cota press, which consists of two side by side interconnected tablet presses where the core is made on one press then mechanically transferred to the next press for compression coating. Each "press" has an independent powder feed mechanism so that core blend is loaded on one machine and coating blend on the other. Mechanical transfer arms rotate between the machines to remove cores from one press and transfer them to the coating press. Other and more modern types of presses which may be used (e.g. Elizabeth Hata HT-AP44-MSU-C, Killian RUD, Fette PT 4090) have a dual feed system for coating blend and pre-made cores. This configuration is more flexible, in that cores can be pan coated with a functional or cosmetic coating before compression coating. However, any conventional, art-recognized manufacturing technique that permits the formulation of a chewable component over a solid dosage form will be readily appreciated by the skilled artisan and is contemplated by the present disclosure.

A similar embodiment would not only have an outer chewable layer, but also a thin shell outside of the chewable layer. This would be similar to the thin candy shell of an M&M candy. With this thin outer shell helping to hold the tablet together, the chewable layer can be designed to more easily crumble and dissolve than if there was no outer shell, e.g., by reducing the amount of binder or by reducing the compression to that which will minimally hold the chewable component together until the outer shell is applied.

The outer shell can be a sugar coating or a polymer coating such as hydroxypropylmethylcelluose or polyvinyl-alcohol or combinations thereof, for example.

Another embodiment contemplated by the present disclosure is an outer layer made from liquid, within a thin outer skin or shell. When the patient bites lightly on the tablet, this outer skin would fracture, allowing the liquid (or gel) of a fast-absorbing medication to release into the mouth and thus be absorbed quickly, starting at the mouth's mucous membranes. There are several possible embodiments of this outer layer, including viscous liquids, gels, quick absorbable substances, powder within a breakable skin, substances that "melt" in the mouth (quickly absorb) and more. In another embodiment of this example, the liquid can be comprised of two or more substances and can also include solid particles which can be comprised of one or more substances. In this embodiment, the solid particles would be suspended in the liquid. The solid particles could also dissolve over time into the liquid.

When the outer layer is manufactured to absorb quickly, the drug can be formulated with a water soluble excipient such as a sugar, sugar alcohol, polyethylene glycol (PEG), or polyethylene oxide. The preferred water-soluble excipients are the sugar alcohols including, but not limited to sorbitol, mannitol, maltitol, reduced starch saccharide, xylitol, reduced paratinose, erythritol, and combinations thereof. The preferred sugar is glucose. Other suitable water-soluble excipients include gelatin, partially hydrolyzed gelatin, hydrolyzed dextran, dextrin, alginate and mixtures thereof. A disintigrating agent such as sodium starch "meltable" formulation can be readily determined by one of skill in the art.

When the outer layer contains a liquid within an outer skin, the outer skin can be gelatin and the drug can be mixed with water or miscible solvents such as propylene glycol; PEG's and ethanol, or an oleaginous medium, e.g., peanut oil, liquid paraffin or olive oil.

Another embodiment has an outer layer which rapidly dissolves when sucked on. When the inner layer is reached, the patient would swallow the tablet. This embodiment can be designed such that the outer surface of the inner, hard layer has a texture that is easily recognized by the tongue, so that it is clear to the patient when the outer layer is fully dissolved, and thus when it is time to swallow the inner layer. This would be similar to a Tootsie Pop®, in that the Tootsie Roll® center is easily recognized by the tongue as feeling very different than the outer dissolvable candy.

In such an embodiment, the dissolvable portion can be formulated in a dissolvable matrix material. The dissolvable matrix may include carbohydrates, fats, proteins, waxes (natural and synthetic), hydrocarbons, and other materials which safely and rapidly dissolve in the mouth.

The inner, swallowable "slow absorb" or "extended release" layer contemplated by the present disclosure can have any number of art-recognized constituencies. In one embodiment, the inner layer is designed similar to a standard tablet. In another embodiment, the inner layer is enteric coated, further slowing the release of the medication. In still another embodiment the inner layer can be an extended release dosage form.

When the inner layer has an enteric coating, the coating can be, e.g., a material selected from the group consisting of one or more of the following: cellulose acetate phthalate, alginates, alkali-soluble acrylic resins, hydroxypropyl methylcellulose phthalate, methacrylate-methacrylic acid copolymers, polyvinyl acetate phthalate and styrol maleic acid copolymers. The coating can also be multilayered; i.e. one or more coatings are contemplated to provide extended release kinetics which permit the inner tablet to release over a period of from 15 minutes to 24 hours or more.

The extended release dosage form can be formulated with the drug dispersed in a matrix or with an extended release coating. Suitable materials form inclusion in an extended release matrix or coating can be, e.g., a cellulosic material, an acrylic polymer, or a combination thereof.

The contemplated inner layer can also be made of a substance which is softer and more pliable than a standard hard tablet, e.g. similar to a hard taffy. In this way, the patient could not chip their teeth when biting the tablet, as the inner layer will absorb some of the shock of the bite without breaking or dissolving. It can then by swallowed to be absorbed in the GI system, after the outer layer was absorbed in the mouth.

The "taffy" can be prepared, e.g., with an admixture of a sugar melt having at least 40% sugar, such as fructose and a surface active agent. However, the skilled artisan can readily prepare alternative formulations of sugar-based substances to achieve an inner core that absorbs the shock of the chewing force exerted by an individual in the normal course of taking a chewable medication.

In another example, the dissolvable portion can include two or more discrete pulverizable portions or layers. All discrete pulverizable layers will be dispersed in the oral cavity by masticating, thereby releasing the layers from the hard inner core.

Compounds which may be included in the two or more discrete pulverizable portions or layers include sodium lauryl sulfate, as well as coloring agents, flavoring agents, sweetening agents (including other nonnutritive sweeteners), tableting agents, stabilizers, antioxidants, cooling agents, and preservatives, suitable water-soluble sugars and/or sugar substitutes including glucose, maltose, sucrose, dextrose, fructose, sorbitol, mannitol or other types of natural or artificial sweeteners, gel forming agents including xanthan gum, methylcelluloses such as sodium carboxymethylcellulose or hydroxypropylmethylcellulose, hydroxyethylcellulose, hydroxypropylcellulose, alginates, tragacanth and soluble starch, binding agents including cellulose, cellulosic derivatives, polyvinyl pyrrolidone, starch, modified starch, and microcrystalline cellulose, water soluble excipients such as a sugar, sugar alcohol, polyethylene glycol (PEG), or polyethylene oxide, sorbitol, mannitol, maltitol, reduced starch saccharide, xylitol, reduced paratinose, erythritol, gelatin, partially hydrolyzed gelatin, hydrolyzed dextran, dextrin, alginate, naproxen sodium (sodium (2S)-2-(6-methoxynaphthalen-2-yl)propanoate) and ibuprofen (2-[4-(2-methylpropyl)phenyl]propanoic acid), aspirin, a COX inhibitor, COX-2 specific inhibitors such as colecoxib (Celebrex™) (4-[5-(4-methylphenyl-3-)trifluoromethyl)pyrazol-1-yl]benzenesulfonamide) and rofecoxib (Vioxx™) (4-(4-methylsulfonylphenyl)-3-phenyl-5H-furan-2-one), Percocet™ (combination of acetaminophen and oxycodone), Tylenol acetaminophen, an NSAID an antiemetic, a sedative, an anesthetic, an amnesiatic, acetaminophen, diclofenac, aspirin, laropiprant, or vitamins such as Vitamin C, and more, or any combination of the above. These discrete layers may also cover only a portion of the hard inner core, or swallowable portion.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Example 1

Intraoral Administration of Aspirin Reduces Fumarate-Induced Flush More than Swallowed Aspirin Seven human patients with multiple sclerosis who were already taking dimethyl fumarate and had experienced flushing side effects from dimethyl fumarate were recruited for this study. Each patient did not have an allergy or reaction to aspirin or dimethyl fumarate (DMF), had not been diagnosed with kidney disease or liver disease, was not pregnant or planning to be pregnant within the following two months, had not been breastfeeding within the preceding two months, and had not used aspirin for the preceding 7 days.

In Period I, each patient was given their standard dose of 240 mg dimethyl fumarate orally. Each patient was asked to rate his or her flush on the Global Flush Severity Scale (GFSS) (see Paolini et al. *Int. J. Clin. Pract.* 62(6):896-904 (2008)), when the flush completely resolved. The Global Flushing Severity Score measures, overall, in the previous 24 hours, how each patient rates the flushing symptoms, including redness, warmth, tingling, and itchiness of the skin.

Period II did not start until at least two days upon completion of Period I. At Period II, each patient orally swallowed 162 mg aspirin followed by 240 mg dimethyl fumarate. After the flush completely resolved, then each patient recorded his or her GFSS flush rating.

Not until at least two days later did Period III start. At Period III, each patient was asked to not swallow the orally administered aspirin (162 mg) but to allow the aspirin to be absorbed through the oral mucosa. The aspirin was in powdered form and the remaining aspirin in the mouth was washed out with water. Afterwards, 240 mg of dimethyl fumarate was swallowed with a glass of water. Still, the flush was rated (GFSS) after it was resolved.

The patients during Period III suffered the least severe flush than during any other Periods. Among Periods I through II, the severity of flush was the lowest in Period III (a 52% reduction as compared to Period I), second lowest in Period II (a 33% reduction as compared to Period I) and the highest in Period I. As the total amount of aspirin was the same between Period II and III, this example therefore demonstrates that oral release of aspirin greatly increased aspirin's anti-flushing effect for dimethyl fumarate.

Example 2

Dose Ranging Study

Two hundred and twenty subjects will be recruited for the purposes of this trial. Eligible patients must have a diagnosis of release-remitting multiple sclerosis (RMMS), and at least one relapse in the 12 months prior to randomization. The trial is a randomized, double-blind, placebo-controlled, dose-ranging trial in RMMS patients already taking DMF. The trial is scheduled to last 48 weeks. Prior to the 48 weeks of on-trial time, patients will be randomly assigned, in a 1:1:1:1:1 allocation, to one of five treatments: (i) DMF 180 mg/VTS-ASA (aspirin) 200 mg twice daily; (ii) DMF 240 mg/VTS-ASA 200 mg twice daily; (iii) DMF 300 mg/VTS-ASA 200 mg twice daily; (iv) DMF 300 mg/VTS-ASA 200 mg once daily; and (v) Placebo 240 mg twice daily. Both patients and practitioners were will be blinded to the treatment regime. Study participants will report to the clinical research unit (CRU) every 4 weeks during the study period for routine medical monitoring, and every 4 weeks for the first 24 weeks for brain MRI scans.

Study participants will be evaluated for the following primary endpoints; (i) Number of new GdE lesions in weeks 12-14; (ii) Number of new GdE lesions in weeks 4-24; (iii) Number of new GdE lesions per patient in weeks 12-24; (iv) ARR during weeks 0-24; (v) ARR during weeks 25-48; (vi) ARR during weeks 0-48. Secondary safety endpoints include; (i) headache; (ii) nasopharyngitis; (iii) nausea; (iv) diarrhea; (v) abdominal pain; (vi) lower limb fracture; (vii) pelvic inflammatory disease; (viii) phlebitis; (ix) urinary retention; and (x) uterine leiomyoma.

In addition to the primary and secondary endpoints listed above, the proposed trial will additionally investigate endpoints that are specific to the inquiry of the effect of pretreatment of aspirin with DMF. These endpoints include; (i) occurrence of flush; (ii) occurrence of pruritus; (iii) occurrence of hot flush; (iv) Global Flushing Severity Score (GFSS); (v) Fatigue Severity Score (FSS); (vi) Number of new or enlarging T2-hyperintense lesions at week 24, a metric of remyelination; (vii) Number of new T1-hypointense lesions at week 24, a metric of remyelination; and (viii) PHQ-9 Depression Score.

Clinically meaningful differences between treatment groups will be evaluated at the end of the study period according to intention to treat (ITT) principals.

Example 3

Bioequivalence Study

The bioequivalence study will be performed in two parts; a pilot study (about 20 healthy subjects), followed by a Phase 1 study (about 125 subjects). The pilot study in healthy males and females is designed to establish a pharmacokinetic (PK) profile under fasting and fed conditions for the orally administered test and reference products to compare the bioavailability in accordance with Food and Drug Administration (FDA) and Center for Drug Evaluation and Research (CDER) guidelines. Phase 1 subjects have a diagnosis of release-remitting multiple sclerosis (RMMS), and at least one relapse in the 12 months prior to randomization.

Subjects in both studies will be randomly assigned, in a 1:1:1:1 allocation, to one of four treatments: oral administration of (i) aspirin only (control); (ii) DMF only; (iii) DMF/aspirin combination in the fasted state; (iv) DMF/aspirin combination in the fed state. Both patients and practitioners will be blinded to the treatment regime.

Study Objectives

To investigate the PK profiles of the test product, DMF 180 mg/ASA 150 mg capsules and the reference products, DMF 240 mg delayed-released capsules and Bayer Aspirin® 325 mg tablets, and to determine the sample size for future studies.

For this purpose the PK profiles of DMF's metabolite, monomethylfumarate (MMF), acetylsalicylic acid (ASA)

and its active metabolite, salicylic acid (SA) in plasma will be investigated after administration of a single dose of the test and reference formulations, under fasting and fed conditions.

These will be a single-dose, open-label, laboratory-blind, randomized, four period crossover pilot study with orally administered dimethylfumarate and aspirin conducted under fasting and fed conditions.

The studies will comprise:

Screening period of maximum 21 days;

Four treatment periods (each of which will include a profile period of 12 hours separated by a wash-out period of 3 calendar days (minimum number of days based on half-life of the analyte/metabolites) to 7 calendar days (maximum number of days based on logistical arrangements) between consecutive administrations of the IMP, and A post-study visit within 72 hours of completion of the last treatment period of the study.

Procedures listed for the post-study visit will be performed in the event of early withdrawal from the study. Subjects will be assigned randomly to treatment sequence, before the first administration of IMP.

The duration of this study is expected to be approximately 25 days (approximately 3½ weeks) per subject (excluding the screening period). The actual overall study duration and study recruitment time may vary.

Along with other assessments during the screening period and admission, during the treatment period the subjects vital signs will be assessed and they will be assessed for adverse events and concomitant medication and pharmacokinetic blood samples will be collected at the following time points: at pre dose (0 hours), at 15 minutes (acetylsalicylic acid and salicylic acid only), 30 minutes, 45 minutes (acetylsalicylic acid and salicylic acid only) and at 1 hour, 1 hour 30 minutes, 2 hours, 2 hours 30 minutes, 3 hours, 3 hours 30 minutes, 4 hours, 5 hours, 6 hours, 7 hours, 8 hours, 10 hours and 12 hours post dose (total: 17 samples per treatment period). If applicable, the collection of PK blood samples take precedence over other assessments at a scheduled time-point.

Subjects will receive either the test or reference product, according to the randomization schedule, under fasting and fed conditions. Subjects will receive each product once.

| Treatment A - DMF only fasting (Reference 1) | |
|---|---|
| API: | Dimethylfumarate (DMF) |
| Dosage form and strength: | 240 mg delayed release capsule |
| Study dose: | 240 mg (1 capsule) |
| Route of administration: | Oral |

| Treatment B - Aspirin only fasting (Reference 2) | |
|---|---|
| API: | Aspirin (acetylsalicylic acid [ASA]) |
| Dosage form and strength: | 325 mg tablet |
| Study dose: | 325 mg (1 tablet) |
| Route of administration: | Oral |

| Treatment C - DMF/aspirin (ASA) fasting (Test 1) | |
|---|---|
| API: | DMF 180 mg/aspirin (ASA) 150 mg |
| Dosage form and strength: | DMF 180 mg/aspirin (ASA) 150 mg fixed dose combination capsule |
| Study dose: | DMF 180 mg/aspirin (ASA) 150 mg capsule (1 capsule) |
| Route of administration: | Oral (the outer layer of the fixed dose combination capsule contains aspirin that dissolves in the mouth before the remaining part of the capsule is then swallowed whole with water) |

| Treatment D - DMF/aspirin (ASA) fed (Test 2) | |
|---|---|
| API: | DMF 180 mg/aspirin (ASA) 150 mg |
| Dosage form and strength: | DMF 180 mg/aspirin (ASA) 150 mg fixed dose combination capsule |
| Study dose: | DMF 180 mg/aspirin (ASA) 150 mg capsule (1 capsule) |
| Route of administration: | Oral (the outer layer of the fixed dose combination capsule contains aspirin that dissolves in the mouth before the remaining part of the capsule is then swallowed whole with water) |

For the fasting treatment periods, after an overnight fast of at least 10 hours, subjects will receive either the reference or the test product (according to the randomization schedule) with 240 mL water. The reference products must be swallowed whole with water. The fixed dose combination capsule) must be kept in the mouth until the outer layer (containing the aspirin) has dissolved in the mouth before the capsule is then swallowed whole with water. Specific details on the administration of the test product will be provided in a separate document, if needed.

For fed treatment period, after an overnight fast of at least 10 hours, subjects will receive a standardized high-fat, high-calorie breakfast 30 minutes before administration of IMP. The entire meal must be consumed within 30 minutes. After completion of the breakfast subjects will receive either the reference or the test product (according to the randomization schedule) with 240 mL water. The reference products must be swallowed whole with water. The fixed dose combination capsule) must be kept in the mouth until the outer layer (containing the aspirin) has dissolved in the mouth before the capsule is then swallowed whole with water.

Quantitative analysis of monomethylfumarate, acetylsalicylic acid and salicylic acid in the collected plasma samples will be performed by BASD using liquid chromatography with tandem mass spectrometry (LC-MS/MS).

Calculation of the PK parameters will be made with Phoenix® WinNonlin® 6.2 (or higher) (Certara, L. P., 1699 South Hanley Road, St Louis, Ms. 63144, USA). The PK parameters will be calculated for each subject and treatment using non-compartmental analysis and using the actual sampling time intervals (relative to IMP administration).

Primary Pharmacokinetic Parameters for monomethylfumarate, acetylsalicylic acid and salicylic acid:

Maximum observed plasma concentration ($C_{max}$)

Area under the plasma concentration versus time curve, from time zero to t, where t is the time of the last quantifiable concentration ($AUC_{(0-t)}$)

Area under the plasma concentration versus time curve, with extrapolation to infinity ($AUC_{(0-\infty)}$)

Secondary Pharmacokinetic Parameters for monomethylfumarate, acetylsalicylic acid and salicylic acid Time to maximum observed plasma concentration ($t_{max}$)

Terminal elimination rate constant ($\lambda_z$)

Apparent terminal elimination half-life ($t_{1/2-z}$)

It is contemplated that this study will show that that by co-administering DMF with aspirin as described herein, the bioavailability of the DMF will be increased such that the effective dose of DMF can be reduced to as low as about 360 mg/day, or 480 mg/day or less, or about 400 mg/day, about 420 mg/day, or from about 360 mg/day to about 420 mg/day.

Example 4

Pilot, Randomized, Open-Label, 2-Way Crossover Comparative Bioavailability Study of Dimethyl Fumarate-Acetylsalicylic Acid 180 mg-150 mg Delayed-Release Capsule (vts-72) and Tecfidera 240 mg Delayed-Release Capsule (reference) following a Single Dose in Healthy Subjects Under Fasting Conditions The objective of this example was to compare the rate and extent of absorption of monomethyl fumarate from a dimethyl fumarate-acetylsalicylic acid 180 mg-150 mg delayed-release capsule (VTS-72) (Test; Treatment A) versus Tecfidera 240 mg delayed-release capsule (Reference; Treatment B), administered as 1×180 mg-150 mg or 1×240 mg delayed-release capsule under fasting conditions.

This was a single center, pilot, comparative bioavailability, open-label, randomized, single-dose, 2-period, 2-sequence, crossover study under fasting conditions. A total of 12 healthy adult male or female volunteers were included in this pilot study. For each period, subjects will be confined from at least 10 hours before dosing until 12 hours post-dose. There were a washout of 7 days or more between doses. The washout period could be increased for logistical considerations. Participation of each subject in this study lasted approximately 9 days. Subjects were administered each treatment according to the 2-period, 2-sequence, block randomization scheme.

Treatment A: Subjects were required not to wear dentures or to remove their tongue piercing at the time of dosing. The delayed-release capsule were placed on the subject's tongue. Subjects were instructed to suck the delayed-release capsule until the acetylsalicylic acid coating was dissolved or up to a maximum of 1 minute after the delayed-release capsule had been placed on the subject's tongue. The delayed-release capsule should not be chewed, bitten, or swallowed during that 1 minute period or until the coating is dissolved; only the saliva could be swallowed. The subject was instructed to give a hand sign once the acetylsalicylic acid coating was dissolved (the capsule should feel and taste different). Thereafter, or up to a maximum of 1 minute after the delayed-release capsule was placed on the subject's tongue, 240 mL of water was given to subjects to swallow the capsule. Time of dosing was set to the time the capsule was placed on the tongue. A hand and mouth check was performed to ensure consumption of the medication.

Treatment B: Study medication was administered to each subject and was swallowed whole with 240 mL of water without being sucked, chewed or bitten, and a hand and mouth check was performed to ensure consumption of the medication.

Flushing (including redness, warmth, tingling, and itchiness of the skin) was assessed at 0.5, 1, 1.5, 2, 2.5, 3, 3.5, and 4 hours post-dose using the question and the rating scale presented in Section-Flushing Assessment below. Half grades were not assigned. Flushing symptoms were recorded as adverse events.

GI symptoms were assessed at 10 hours post-dose using the questions and the rating scale presented in Section-Gastrointestinal Symptoms Assessment below. Half grades were not assigned. GI symptoms were recorded as adverse events.

Flushing Assessment

Flushing was assessed using the question below. The question was asked by the clinical staff:

Question 1: Overall, at this moment, how would you rate your flushing symptoms (including redness, warmth, tingling, and itchiness of the skin)? Score from 0 to 10 (none 0, mild 1 to 3, moderate 4 to 6, severe 7 to 9, extreme 10).

FIG. 1 is an example of the scale that was used to rate the assessment of Question 1.

Gastrointestinal Symptoms Assessment

Gastrointestinal symptoms were assessed using the questions below. Questions were asked by the clinical staff:

Question 2: Overall, during the past 10 hours, how would you rate your GI side effects (nausea, diarrhea, upper abdominal pain, lower abdominal pain, vomiting, indigestion, constipation, bloating, and flatulence)?

Question 3: Overall, during the past 10 hours, how bothersome were your GI side effects (nausea, diarrhea, upper abdominal pain, lower abdominal pain, vomiting, indigestion, constipation, bloating, and flatulence)?

Figure 2:
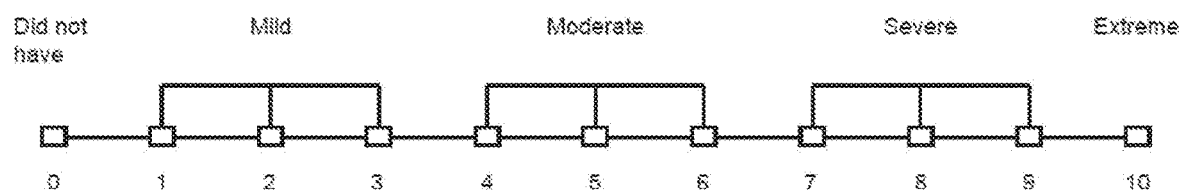
FIG. 2 is an example of the scale that was used to rate the assessment of Questions 2 and 3 in Example 4.

FIG. 2 is an example of the scale that was used to rate the assessment of Questions 2 and 3.

The flushing side effect reported by each of the subject is summarized in Table 1 below. The total reduction of flushing from 15.9 to 7.9 was about 50.3%. When the doses of DMF were normalized to 180 mg in both treatments, the reduction was still 33.6%. Considering that, as shown below, aspirin increased the bioavailability of DMF by about 5%, the reduction of the flushing side effect is actually about 36.8%. Also interestingly, 6 of these 11 subjects had their flushes peak at least 30 mins earlier with VTS-72 (only 2 were later) than with DMF alone.

TABLE 1

Summary of Flush Ratings

| | Total Flush Rating* | |
| --- | --- | --- |
| Subject # | Treatment B (240 mg DMF) | Treatment A (180 mg DMF + 150 mg Aspirin) |
| 1 | (drop out) | (drop out) |
| 2 | 26 | 5 |
| 3 | 8 | 8 |
| 4 | 18 | 14 |
| 5 | 26 | 13 |
| 6 | 14 | 6 |
| 7 | 36 | 13 |
| 8 | 8 | 2 |
| 9 | 11 | 9 |
| 10 | 9 | 0 |
| 11 | 8 | 15 |
| 12 | 11 | 2 |
| Mean | 15.9 | 7.9 |
| Normalized Mean | 11.9 | 7.9 |

*Flushes were scored from 0-10 every 30 mins, up to 4 hours post dose (8 total measurements per dose) and added up Table 2 below provides a descriptive statistics summary of monomethyl fumarate plasma pharmacokinetic parameters.

TABLE 2

Descriptive Statistics Summary of Monomethyl Fumarate Plasma Pharmacokinetic Parameters

| Parameter (units) | Treatment A | | | | Treatment B | | | |
|---|---|---|---|---|---|---|---|---|
| | N | Mean | SD | CV % | N | Mean | SD | CV % |
| $AUC_{0-t}$ (h*ng/mL) | 11 | 3874.01 | 1213.13 | 31.31 | 11 | 4924.24 | 1550.02 | 31.48 |
| $AUC_{0-inf}$ (h*ng/mL) | 11 | 3885.63 | 1214.97 | 31.27 | 11 | 4958.99 | 1544.26 | 31.14 |
| Residual area (%) | 11 | 0.32 | 0.16 | 49.93 | 11 | 0.74 | 1.79 | 243.23 |
| $C_{max}$ (ng/mL) | 11 | 2034.02 | 599.26 | 29.46 | 11 | 2749.40 | 988.79 | 35.96 |
| $T_{1/2\ el}$ (h) | 11 | 0.62 | 0.14 | 22.14 | 11 | 0.75 | 0.27 | 35.53 |
| $K_{el}$ (/h) | 11 | 1.1618 | 0.2268 | 19.5244 | 11 | 1.0149 | 0.2926 | 28.8326 |
| Correlation | 11 | −0.9978 | 0.0023 | −0.2328 | 11 | −0.9639 | 0.0689 | −7.1439 |
| $K_{el\ Lower}$ (h) | 11 | 4.768 | 0.959 | 20.105 | 11 | 5.364 | 1.002 | 18.687 |
| $K_{el\ Upper}$ (h) | 11 | 7.269 | 1.349 | 18.553 | 11 | 8.360 | 1.362 | 16.287 |

When the mean values in both treatments were normalized to 180 mg DMF, the mean values are summarized in Table 3. Co-administration of aspirin did not have significant impact on the $C_{max}$ of DMF. However, the co-administration of aspirin caused an about 5% increase in $AUC_{0-t}$ and $AUC_{0-inf}$. Also surprisingly, the data showed very tight inter-subject variability (confidence intervals).

TABLE 3

Statistics Summary after Dose Normalization

| | Treatment A | Treatment B (normalized) | Change % (A over B) |
|---|---|---|---|
| $AUC_{0-t}$ (h*ng/mL) | 3874.01 | 3693.18 | 4.90% |
| $AUC_{0-inf}$ (h*ng/mL) | 3885.63 | 3719.2425 | 4.47% |
| Residual area (%) | 0.32 | 0.555 | −4.23% |
| $C_{max}$ (ng/mL) | 2034.02 | 2062.05 | −1.36% |

Also interestingly, even though the $C_{max}$ did not have a significant change, the co-administration of aspirin shifted the $T_{max}$ to about 20 minutes earlier (median). See Table 4.

TABLE 4

Summary Statistics of $T_{max}$

| Parameter (units) | Treatment A | | | | Treatment B | | | |
|---|---|---|---|---|---|---|---|---|
| | N | Median | Min | Max | N | Median | Min | Max |
| $T_{max}$ (h) | 11 | 2.330 | 1.327 | 4.499 | 11 | 2.661 | 0.747 | 4.994 |

This example demonstrates that co-administration of aspirin increased the bioavailability of DMF by about 5% while at the same time reducing the flushing side effect by more than 35%.

Unless otherwise defined, all technical and scientific terms used herein have the same meaning as commonly understood by one of ordinary skill in the art to which this disclosure belongs.

The disclosures illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

Thus, it should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

What is claimed is:

1. A dosage form comprising an effective amount of aspirin and an effective amount of fumaric acid or an ester or a salt thereof, wherein the aspirin and fumaric acid or an ester or a salt thereof are each individually formulated as enterically coated microspheres.

2. The dosage form of claim 1, wherein the enterically coated microspheres are formulated such that the aspirin and fumaric acid or an ester or a salt thereof are released in the gastrointestinal tract at substantially the same time.

3. The dosage form of claim 1, wherein the enterically coated microspheres comprising aspirin are formulated such that the aspirin is released in the gastrointestinal tract within about one to 20 minutes prior to the fumaric acid or an ester or a salt thereof is released in the gastrointestinal tract.

4. The dosage form of claim 1, wherein the fumaric acid or an ester or a salt thereof is dimethyl fumarate.

5. The dosage form of claim 1, wherein the dosage form consists essentially of an effective amount of aspirin and an effective amount of dimethyl fumarate.

6. The dosage form of claim 1, comprising from about 80 mg to about 450 mg of dimethyl fumarate.

7. The dosage form of claim 1, wherein the enterically coated microspheres comprising aspirin comprise from about 20 mg to about 500 mg of aspirin.

8. An enteric coated capsule comprising the dosage form of claim 1.

9. The capsule of claim 8, wherein the capsule is further coated with a second dose of aspirin formulated to dissolve in an oral cavity of a subject.

10. The capsule of claim 9, wherein the second dose of aspirin is from about 20 mg to about 500 mg.

11. A capsule comprising a dosage form comprising an effective amount of aspirin and an effective amount of fumaric acid or an ester or a salt thereof, wherein the aspirin and fumaric acid or an ester or a salt thereof are each individually formulated as enterically coated microspheres contained within the capsule shell.

12. The capsule of claim 11, wherein the capsule is coated with a second dose of aspirin formulated to dissolve in an oral cavity of a subject.

13. The capsule of claim 12, comprising from about 20 mg to about 500 mg of aspirin.

14. The dosage form of claim 1, which comprises 75 mg to 325 mg aspirin and 150 mg to 225 mg of the fumaric acid or an ester or a salt thereof.

15. The dosage form of claim 1, which comprises 75 mg to 325 mg aspirin and 150 mg to 225 mg of dimethyl fumarate.

16. The dosage form of claim 15, further comprising a portion of aspirin which is formulated to dissolve in an oral cavity of a subject.

17. The dosage form of claim 1, which comprises 150 mg to 650 mg aspirin and 300 mg to 450 mg of dimethyl fumarate.

18. The dosage form of claim 17, further comprising a portion of aspirin which is formulated to dissolve in an oral cavity of a subject.

* * * * *